United States Patent [19]

Shinmoto

[11] Patent Number: 4,596,997
[45] Date of Patent: Jun. 24, 1986

[54] PHENOLIC COMPOUND, PREPARATION THEREOF AND RECORDING MATERIAL EMPLOYING SAME

[75] Inventor: Masaki Shinmoto, Yono, Japan

[73] Assignee: Nippon Kayaku Kabushiki Kaisha, Tokyo, Japan

[21] Appl. No.: 696,913

[22] Filed: Jan. 31, 1985

[30] Foreign Application Priority Data

Feb. 14, 1984 [JP] Japan .................................. 59-24311
Apr. 2, 1984 [JP] Japan .................................. 59-63277

[51] Int. Cl.⁴ ...................... B41M 5/18; C07C 147/10
[52] U.S. Cl. ...................................... 346/216; 568/33; 346/225
[58] Field of Search ................... 568/33; 346/216, 225

[56] References Cited

U.S. PATENT DOCUMENTS

| | | | |
|---|---|---|---|
| 3,539,375 | 11/1970 | Baum | 117/36.2 |
| 4,370,370 | 1/1983 | Iwata et al. | 428/40 |
| 4,388,362 | 6/1983 | Iwata et al. | 428/211 |
| 4,420,538 | 12/1983 | Nakamura et al. | 428/411 |
| 4,511,910 | 4/1985 | Taniguchi et al. | 346/216 |

FOREIGN PATENT DOCUMENTS 43-4160  2/1968  Japan.

OTHER PUBLICATIONS

S. Prajapati et al., Chem. Abstracts 89:108953q (1978), Studies on 4,4'-Dihydroxydiphenyl Sulfone and 4,4'-Dihydroxydiphenyl Ether.

O. Fedotova et al., Chem. Abstracts: 78: 159124a (1973), Synthesis and Study of Unsaturated Dicarboxylic Ether Acids.

*Primary Examiner*—Donald G. Daus
*Assistant Examiner*—M. E. Ceperley

[57] ABSTRACT

A phenolic compound represented by the formula:

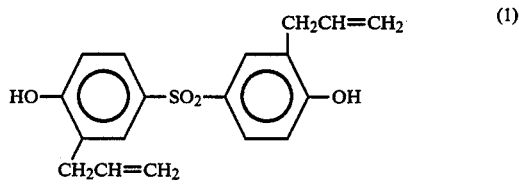

a process for producing it and a recording material comprising a support bearing a heat- or pressure-sensitive color-forming layer containing the phenolic compound and a leuco dye.

1 Claim, No Drawings

PHENOLIC COMPOUND, PREPARATION THEREOF AND RECORDING MATERIAL EMPLOYING SAME

DETAILED DESCRIPTION OF THIS INVENTION

The present invention relates to a novel phenolic compound, a process for producing it and a heat-or pressure-sensitive recording material containing the phenolic compound. More particularly, the present invention relates to a phenolic compound, bis(3-allyl-4-hydroxyphenyl) sulfone, represented by the formula:

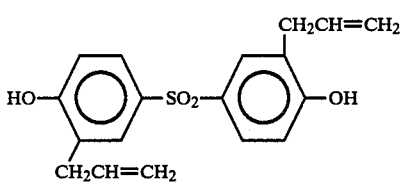    (1)

and to a process for producing the phenolic compound by reacting a compound represented by the formula:

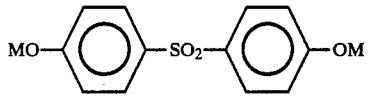    (2)

wherein M represents a hydrogen atom or an alkali metal, with a compound represented by the formula:

$CH_2=CHCH_2-X$    (3)

wherein X represents a halogen atom or an $RSO_3$ group, wherein R represents a substituted or unsubstituted phenyl group or a lower alkyl group, and rearranging the product represented by the formula:

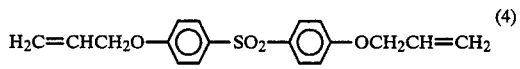    (4)

and a heat- or pressure-sensitive recording material comprising a support bearing a heat- or pressure-sensitive color-forming layer containing the phenolic compound and a leuco dye.

Thermal recording sheets according to a thermal color-forming reaction between a colorless to pale color leuco dye and a phenol or an organic acid were disclosed in Japanese Patent Publications Nos. 4160/1968 and 14039/1970 and have had widespread use. These thermal recording sheets are ones which can be prepared by finely dividing each of a leuco dye (as a color former) and a phenol or an organic acid (as a developer) to form dispersions, mixing the both together, adding adjuvants such as a binder, sensitizer, filler and lubricant to the mixture to form a coating solution, and coating a support such as paper, film or synthetic paper with the coating solution, and which can form colored recording by a chemical reaction which takes place when one or both of the leuco dye and the developer are molten by heating and contacted each other. A thermal printer equipped with a built-in thermal head, for example, is used to heat the thermal recording sheet for its color formation. This thermal recording process has such characteristics as compared with other recording processes that (1) it makes no noise during recording, (2) it can dispense with development, fixation, etc., (3) it is maintenance-free, and (4) the apparatus is relatively inexpensive, and therefore this recording process has been widely used in the fields of printers for facscimiles, computers, electronic calculators, recorders for medical measurements, automatic ticket vending machines, thermal recording labeles, etc.

However, this thermal recorded image obtained by contact between a leuco dye and a developer has various drawbacks in that (1) the image fades when exposed to water or kept immersed in water (water resistance), (2) the image fades markedly at high humidity under a high temperature (moisture resistance), and (3) the image fades or disappears when contacted with a plasticizer, fat or oil (plasticizer resistance). Meanwhile, fields of thermal recordings which are particularly necessary for water resistance, moisture resistance, and plasticizer resistance include thermal recording paper for passenger tickets, medical measurement and POS (Point of Sale) labeles.

Although a variety of processes have heretofore been proposed to improve the above-mentioned resistances no satisfactory process has been obtained yet.

As a result of extensive studies on a process for obtaining a thermal recording (an image) which has improved water resistance, moisture resistance and plasticizer resistance, the inventor of the present invention has found that a thermal recording material containing a leuco dye and bis(3-allyl-4-hydroxyphenyl) sulfone represented by formula (1) can give a recorded image which is extremely excellent in water resistance, moisture resistance and plasticizer resistance, and have achieved this invention.

The phenolic compound of the present invention, i.e. bis(3-allyl-4-hydroxyphenyl) sulfone, can be synthesized by step 1 comprising reacting a 4,4'-sulfonyldiphenol or its alkali metal salt of formula (2) with an allyl compound of formula (3) in water, an organic solvent or a water/organic solvent mixture in the presence of, if necessary, an acid binding agent to form an ether compound (4):

step 1

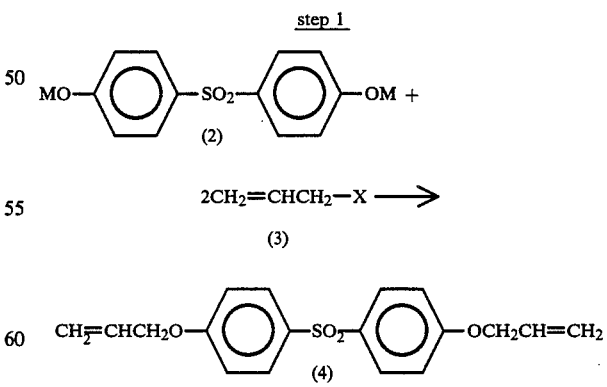

wherein M and X are as defined above, and step 2 comprising thermally rearranging said ether compound (4) in the presence or absence of a solvent:

step 2

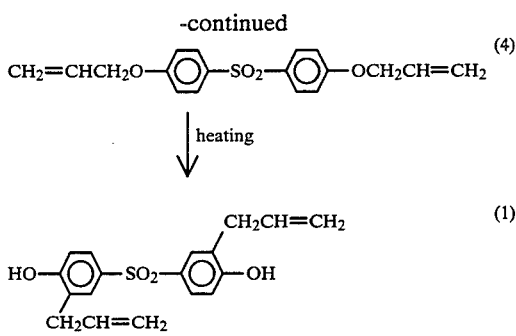

Examples of the allyl compounds (3) used in step 1 include allyl chloride, allyl bromide, allyl iodide, allyl p-toluenesulfonate, allyl benzenesulfonate and allyl methanesulfonate, while those of the reaction solvents used in step 1 include water, alcohols such as methanol, ethanol, isopropyl alcohol and methylcellosolve, polar aprotic solvents such as dimethylformamide, dimethylacetamide, dimethyl sulfoxide, N-methylpyrrolidone and hexamethylphosphoramide, ketones such as acetone, methyl ethyl ketone and methyl isobutyl ketone, aromatic solvents such as benzene, toluene, xylene, chlorobenzene, dichlorobenzene and trichlorobenzene, alkyl halides such as chloroform, dichloromethane and 1,2-dichloroethane, or mixtures thereof.

When a solvent which is insoluble or difficultly soluble in water is used as the organic solvent in a water/organic solvent system, it is preferable to use a phase transfer catalyst as a reaction accelerator. Examples of the reaction accelerators which can be used include benzyltriethylammonium chloride, benzyltributylammonium chloride, tetrabutylammonium bromide, trioctylmethylammonium chloride, N-laurylpyridinium chloride, N-lauryl-4-picolinium chloride, mixed N-benzyl picolinium chloride, benzyltrimethylammonium chloride and benzyltriethylammonium hydroxide.

The acid binding agents which can be used include, for example, inorganic bases such as caustic soda, caustic potash, sodium carbonate, pottasium carbonate, calcium carbonate, magnesium oxide, zinc oxide, calcium oxide, magnesium hydroxide, zinc hydroxide and calcium hydroxide, and alkali or alkaline earth metal salts of an organic acid such as sodium acetate and pottasium acetate.

The 4,4'-sulfonyldiphenol may be reacted with the allyl compound at a molar ratio in the range of 1:2 to 1:8, particularly desirably 1:2 to 1:4.

The reaction temperature may be 20° to 150° C., and the reaction time may be 1 to 20 hours. The produced ether compound of formula (4) may be used in the subsequent step 2 after separation or in the form of the liquid reaction mixture itself.

It is preferable that the rearrangement reaction in step 2 is performed at a temperature of 150° C. or above, especially in the range of 170° to 230° C. The rearrangement reaction can proceed by heating in the presence or absence of an organic solvent. Examples of the organic solvents which can be used in the rearrangement reaction include aromatic solvents such as dichlorobenzenes, trichlorobenzenes and pseudooumene, anilines such as dimethylaniline and diethylaniline, polar aprotic solvents such as dimethyl sulfoxide and N-methylpyrrolidone, and alcohols such as octyl alcohol, and preferred organic solvents are those having a boiling point of 160° C. or above.

When the liquid reaction mixture formed in the etherification is subjected directly to the rearrangement reaction and the solvent used in the etherification is a low-boiling one, the temperature of the reaction mixture at the rearrangement reaction may be increased while the solvent is being distilled off, and the rearrangement reaction may be also performed in the absence of any solvent or after adding a solvent for the rearrangement. When a solvent which can be used in the rearrangement reaction as described above is also used in the etherification reaction, the reaction mixture can be heated to a higher temperature enough to effect the rearrangement reaction.

The phenolic compound of the present invention thus produced can be isolated either by dissolving it in an aqueous alkali solution and precipitating it with an acid, or by crystallizing the compound from a solvent after the rearrangement reaction. In both cases, the objective product can be obtained without any trouble in quality.

The phenolic compound of the present invention is characterized in that when it is used as a developer in a heat- or pressure-sensitive recording process comprising a combination of a color-former with a developer, it can give a colored recorded image having extremely excellent resistant to water, moisture and plasticizer.

The phenolic compound of formula (1) can be also used in a variety of applications or as starting materials set forth below:

(1) starting materials for epoxy resins, polycarbonate resins, polyester phenolic resins, polyether sulfone, polyurethane, polyamide resins, ion exchange resins, etc.

(2) polymer additives such as flame retardants, plasticizers, curing agents, stabilizers, or coupling agents, or starting materials therefor, (3) fixing agents for polyamide or cotton fibers, and starting materials for synthetic tannin used in leather tanning agents, dye dispersing agents, waste water treating agents or the like, (4) binders for pigments, photographic chemicals, or electrostatic toners, or starting materials for waxes, varnishes, lacquers, drugs and pesticides, (5) starting materials for preparing flexographic ink, or offset printing ink, and (6) additives used in plating such as acid tin plating, solder plating, or starting materials therefor.

In the present invention, the compound (1) may be used alone or together with one or more of the developers mentioned hereinafter. The developers which can be used include, for example, phenolic compounds such as p-octylphenol, p-tert-butylphenol, p-phenylphenol, 1,1-bis(p-hydroxyphenyl)propane, 2,2-bis(p-hydroxyphenyl)propane, 1,1-bis(p-hydroxyphenyl)cyclohexane, 4,4'-thiobisphenol and 4,4'-sulfonyldiphenol, and aromatic carboxylic acids or their polyvalent metal salts such as benzyl p-hydroxybenzoate, ethyl p-hydroxybenzoate, dibenzyl 4-hydroxyphthalate, dimethyl 4-hydroxyphthalate, ethyl 5-hydroxyisophthalate, 3,5-di-tert-butylsalicylic acid and 3,5-di-α-methylbenzyl-salicylic acid.

Examples of the colorless or pale color leuco dyes which can be used in the present invention include xanthene compounds, triarylmethane compounds, spiropyran compounds, diphenylmethane compounds and thiazine compounds. Particular examples of these dyes include xanthene compounds exemplified by Rhodamine-B anilinolactam, Rhodamine (p-nitroanilino) lactam, 2-dibenzylanino-6-diethylaminofluoran, 2-anilino-3-methyl-6-diethylaminofluroan, 2-anilino-3-methyl-6-cyclohexylmethylaminofluoran, 2-anilino-3-methyl-6-isopentylethylaminofluoran, 2-anilino-3-methyl-6-dibutylanilinofluoran, 2-p-chloroanilino-3-methyl-6-diethylaminofluoran, 2-p-fluoroanilino-3-methyl-6-diethylaminofluoran, 2-p-fluoroanilino-3-methyl-6-dibutylaminofluoran, 2-anilino-3-methyl-6-(p-toluidinoethyl)aminofluoran, 2-p-toluidino-3-methyl-6-diethylaminofluoran, 2-o-chloroanilino-6-diethylfluoran, 2-o-chloroanilino-6-dibutylaminofluoran, 2-o-fluoroanilino-6-dibutylaminofluoran, 2-m-chloroanilino-6-diethylaminofluoran, 2-anilino-3-methyl-6-piperidinofluoran, 2-anilino-3-methyl-6-pyrrolidinofluoran, 2-m-trifluoromethylanilino-6-diethylaminofluoran, 2-dihexylamino-6-diethylaminofluoran, 2-butylamino-3-chloro-6-diethylaminofluoran, 2-ethoxyethylamino-3-chloro-6-diethylaminofluoran, 2-anilino-3-chloro-6-diethylaminofluoran, 2-diphenylamino-6-diethylaminofluoran, 2-anilino-3-methyl-6-diphenylaminofluoran, 2-phenyl-6-diethylaminofluoran, 2-chloro-3-methyl-6-diethylaminofluorn, 2-chloro-6-diethylaminofluoran, 2-methyl-6-diethylaminofluoran, and 6-diethylamino-1,2-benzofluoran; triarylmethane compounds exemplified by 3,3-bis(p-dimethylaminophenyl)-6-dimethylaninophthalide (so-called Crystal Violet Lactone), 3,3-bis(p-dimethylaminophenyl)phthalide, 3-6(p-dimethylaminophenyl)-3-(1,2-dimethylaminoindol-3-yl)-phthalide 3-(p-dimethylaminophenyl)-3-(2-methylindol-3-yl)phthalide, and chromene; spiropyran compounds exemplified by 3-methylspirodinaphthopyran, 3-ethylspirodinaphthopyran, 3,3'-dichlorospirodinaphthopyran, 3-benzylspirodinaphthopyran, 3-methylnaphto-(3-methoxybenzo)-spiropyran, 3-propylspirodibenzopyran, 1,3,3-trimethyl-6'-nitro-8'-methoxyspiro(indoline-2,2'-benzopyran), and 1,3,3-trimethyl-6'-nitrospiro(indoline-2,2'-benzopyran); diphenylmethane compounds exemplified by 4,4'-bisdimethylaminobenzohydrin benzyl ether, N-halophenylleucoauramine, and N-2,4,5-trichlorophenylleucoauramime; thiazine compounds exemplified by Benzoyl Leuco Methylene Blue, and p-Nitrobenzyl Leuco Methylene Blue. These leuco dyes may be used alone or as mixtures thereof.

In addition, binders, sensitizers, fillers, etc., may be suitably used for the preparation of the thermal recording material of the present invention.

Examples of the binders which can be used include methylcellulose, hydroxyethylcellulose, carboxymethylcellulose, polyvinyl alcohol, carboxyl group-modified polyvinyl alcohol, polyvinylpyrrolidone, polyacrylamide, polyacrylic acid, starch or its derivative, casein, gelatin, alkali salts of styrene/maleic anhydride copolymers, water-soluble alkali salts of iso(or diiso)-butylene/maleic anhydride copolymers, or aqueous emulsions of polyvinyl acetate, vinyl chloride/vinyl acetate copolymer, polystyrene, polyacrylate, polyurethane, styrene/butadiene/acrylic monomer copolymer, or the like.

Examples of the sensitizers include higher fatty acid amide such as stearamide, animal waxes such as beeswax and shellack wax, vegetable waxes such as carnauba wax, mineral waxes such as montan wax, paraffin wax, petroleum wax, higher fatty acid esters, higher amine fatty acid/amine condensates, chlorinated paraffin, synthetic paraffin, acetacetanilide, diphenylamines, carbazoles, fatty acid anilides, carboxylates such as dimethyl terephthalate and diphenyl phthalate, sulfonamides such as benzenesulfonanilide, sulfonate such as phenoxyethyl p-toluenesulfonate and phenyl benzenesulfonate, diphenyl sulfones such as bis(4-allyloxyphenyl) sulfone and bis(4-pentylphenyl) sulfone, benzotriazoles, benzophenones, carbonates such as diphenyl carbonate, naphthol derivatives such as 1-benzyloxynaphthalene and 2-benzoyloxynaphthalene, urea derivatives such as N-stearylurea, and diketone compounds such as 4-acetylacetophenone and octadecane-2,-17-dione. Examples of the fillers include calcium carbonate, magnesium carbonate, magnesium oxide, silica, talc, alumina, magnesium hydroxide, aluminum hydroxide, barium sulfate, aluminum stearate, styrene resin, and urea/formalin resin. In addition, a lubricant such as zinc stearate or calcium stearate, a surfactant, a defoaming agent, etc., are added, if required.

The thermal recording material of the present invention can be produced by finely dividing separately each of leuco dyes and the phenolic compound of formula (1) to form dispersions, mixing the both together, adding, if necessary, the above-mentioned components to the mixture to obtain a coating solution for forming a heat-sensitive layer, coating a suitable support such as paper, synthetic paper, or plastic film with the coating solution, and drying the solution and can be used as a thermal recording sheet which is excellent in water, moisture and plasticizer resistances.

A pressure-sensitive recording material using the phenolic compound of formula (1), a leuco dye, etc. is also prepared according to usual methods.

Examples of the present invention will now be described, but it should be noted that the present invention is by no means limited thereto. In the examples, part(s) is(are) given part(s) by weight.

EXAMPLE 1

A flask was charged with 150 parts of water, 150 parts of toluene, 12 parts of caustic soda, and 25 parts of 4,4'-sulfonyldiphenol, and the resulting mixture was dissolved completely to form a solution. To this solution were added 1 part of trioctylmethylammonium chloride (a phase transfer catalyst) and then 36.3 parts of allyl bromide. The resulting solution was reacted at 50° to 60° C. for 15 hours, and toluene was steam-distilled to obtain pale yellow crystals. After filtration, the crystals were washed with 100 parts of methanol to obtain white crystals of bis(4-allyloxyphenyl) sulfone of formula (4). Yield: 30.5 parts (91.2%), m.p.: 143° to 146° C.

15 parts of the obtained bis(4-allyloxyphenyl) sulfone were added to 30 parts of trichlorobenzene, and the mixture was heated at 216° to 219° C. for 10 hours (rearrangement). After completion of the rearrangement, the phenolic product was extracted by adding 50 parts of water and 12 parts of 48%-caustic soda. After purification through active carbon, the water phase was treated with an acid to obtain white crystals of bis(3-allyl-4-hydroxyphenyl) sulfone of formula (1).

Yield: 14.0 parts (93.3%), m.p.: 139°–144° C.

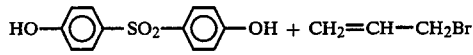

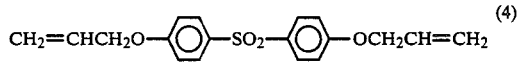

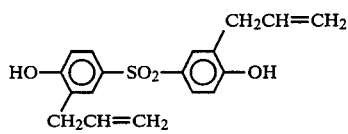

Compounds of formulas (4) and (1) were analyzed to confirm their structures by means of NMR, mass spectroscopy and elementary analysis.

EXAMPLE 2

A flask was charged with 100 parts of DMF, 25 parts of 4,4'-sulfonyldiphenol, 15.2 parts of potassium carbonate and 44.5 parts of allyl p-toluenesulfonate, and the mixture was stirred at 110° to 120° C. for 8 hours. While DMF was being distilled off, the reaction mixture was heated and stirred at 200° to 220° C. for 6 hours. After adding 60 parts of TCB (Triohlorobenzene), the resulting solution was cooled to room temperature under agitation. After filtration, precipitated crystals were thoroughly washed to obtain faintly pale green bis(3-allyl-4-hydroxyphenyl) sulfone. Yield: 30.4 parts (92.1%)

EXAMPLE 3

Mixtures having the following compositions were each ground separately to an average particle diameter of 1 to 3μ by means of a sand grinder to obtain dispersions [A] and [B].

| Dispersion [A] | |
|---|---|
| 2-anilino-3-methyl-6-diethylaminofluoran | 15.0 parts |
| Gosenol GL-05H (polyvinyl alcohol, 25% aqueous solution) (a product of Nippon Gosei Co., Ltd.) | 12.0 parts |
| water | 33.0 parts |
| Dispersion [B] | |
| bis(3-allyl-4-hydroxyphenyl) sulfone | 34.5 parts |
| Gosenol GL-05H (25% aqueous solution) | 22.0 parts |
| water | 110.0 parts |

Further, a mixture of the following composition was ground for 2 hours by means of a sand grinder to obtain dispersion [C].

| Dispersion [C] | |
|---|---|
| Armide HT-P (stearamide, a product of Lion Akzo Co., Ltd.) | 29.5 parts |
| calcium carbonate | 60.0 parts |
| Gosenol GL-05H (25% aqueous solution) | 20.0 parts |
| water | 109.0 parts |

These dispersions were mixed together at dispersion [A]:dispersion [B]:dispersion [C]:ratio of 6:47:47 to obtain a coating solution for forming a heat-sensitive color-forming layer. This solution was applied to paper weighing about 50 g/m$^2$ so that the dry content may be 5 g/m$^2$, and dried to obtain the thermal recording sheet of the present invention.

EXAMPLES 4 THROUGH 9

Thermal recording sheets were obtained by the manner which was the same as that in Example 3 except that each of the leuco dyes shown in Table 1 was used instead of 2-anilino-3-methyl-6-diethylaminofluoran used in Example 3.

COMPARATIVE TEST 1

A comparative thermal recording sheet was obtained by the manner which was the same as that in Example 3 except that the following solution [D] was used instead of dispersion [B] in Example 3.

| Solution [D] | |
|---|---|
| bisphenol A | 34.5 parts |
| Gosenol GL-05H (25% aqueous solution) | 20.0 parts |
| water | 110.0 parts |

COMPARATIVE TEST 2 THROUGH 7

Comparative thermal recording sheets were obtained by the manner which was the same as that in Comparative Test 1 except that each of the leuco dyes shown in Table 1 was used instead of 2-anilino-3-methyl-6-diethylaminofluoran used in Comparative Test 1.

A color formation test and a fastness test were made on the present invention and comparative thermal recording sheets obtained above. The results are shown in Table 1.

TABLE 1

| | Leuco dye used | Color formation test | Fastness test Water resistance | Fastness test Moisture resistance | Fastness test Plasticizer resistance |
|---|---|---|---|---|---|
| Ex. 3 | 2-anilino-3-methyl-6-diethylaminofluoran | 1.32 | 88.6% | 97.7% | 100% |
| Comp. Ex. 1 | 2-anilino-3-methyl-6-diethylaminofluoran | 1.35 | 67.4% | 79.2% | 82.2% |
| Ex. 4 | 2-anilino-3-methyl-6-cyclohexylmethylaminofluoran | 1.29 | 89.1% | 98.4% | 101.6% |
| Comp. Ex. 2 | 2-anilino-3-methyl-6-cyclohexylmethylaminofluoran | 1.34 | 66.4% | 85.8% | 76.1% |
| Ex. 5 | 2-anilino-3-methyl-6-isopentylethylfluoran | 1.29 | 86.8% | 96.9% | 100.8% |
| Comp. Ex. 3 | 2-anilino-3-methyl-6-isopentylethylfluoran | 1.32 | 65.1% | 82.8% | 65.9% |
| Ex. 6 | 2-(o-chloroanilino)-6-diethylaminofluoran | 1.21 | 90.9% | 95.9% | 98.3% |
| Comp. Ex. 4 | 2-(o-chloroanilino)-6-diethylaminofluoran | 1.29 | 62.8% | 36.4% | 47.3% |
| Ex. 7 | 2-(o-fluoroanilino)-6-diethylaminofluoran | 1.14 | 88.2% | 95.0% | 107% |
| Comp. Ex. 5 | 2-(o-fluoroanilino)-6- | 1.27 | 59.8% | 36.2% | 44.9% |

TABLE 1-continued

|  | Leuco dye used | Color formation test | Fastness test | | |
| --- | --- | --- | --- | --- | --- |
|  |  |  | Water resistance | Moisture resistance | Plasticizer resistance |
| Ex. 8 | diethylaminofluoran 2-(o-fluoroanilino)-6-dibutylaminofluoran | 1.30 | 92.3% | 96.9% | 102.3% |
| Comp. Ex. 6 | 2-(o-fluoroanilino)-6-dibutylaminofluoran | 1.34 | 70.9% | 87.3% | 67.1% |
| Ex. 9 | Crystal Violet Lactone | 1.44 | 97.1% | 98.0% | 96.1% |
| Comp. Ex. 7 | Crystal Violet Lactone | 1.40 | 49.1% | 84.6% | 52.9% |

(1) Color formation test

A Roseaster tester was used. A recording sheet was pressed at 140° C. for 5 seconds, and the developed color density was measured by Macbeth densitometer RD-914.

(2) Fastness test

Water resistance: A colored thermal sheet was immersed in 1 l of water for 15 hours, and the color density was measured. The water resistance was calculated according to the formula:

(density after immersion/density before immersion)×100(%).

The higher the value is, the better the resistance is.

Moisture resistance: A color formed thermal sheet was allowed to stand for 24 hours at 60° C. under saturated steam pressure, and the color density was measured. The moisture resistance was calculated according to the formula:

(density after allowing to stand/density before allowing to stand)×100(%).

The higher the value is the better the resistance is.

Plasticizer resistance: A color formed thermal sheet was laid on a polyvinyl chloride wrap and allowed to stand under pressure at room temperature for 7 days. The color density was measured and the plasticizer resistance was calculated according to the formula:

(density after standing/density before standing)×100(%).

The higher the value is, the better the resistance is.

Table 1 clearly shows that the recording materials of the present invention had high color densities, and the developed color images were excellent in water, moisture, and plasticizer resistances.

What we claim is:

1. A thermal recording material comprising
   (a) a support sheet;
   (b) a heat-sensitive color forming lyaer formed on the said support sheet, said heat-sensitive color forming layer comprising a colorless to pale color leuco dye and an amount of bis(3-allyl-4-hydroxyphenyl) sulfone capable of coloring said leuco dye; and
   (c) a binder.

* * * * *